United States Patent [19]
Kangas et al.

[11] Patent Number: 5,680,866
[45] Date of Patent: Oct. 28, 1997

[54] ARTIFICIAL NEURAL NETWORK CARDIOPULMONARY MODELING AND DIAGNOSIS

[75] Inventors: Lars J. Kangas; Paul E. Keller, both of Richland, Wash.

[73] Assignee: Battelle Memorial Institute, Richland, Wash.

[21] Appl. No.: 625,025

[22] Filed: Mar. 29, 1996

[51] Int. Cl.[6] ................................................. A61B 5/0205
[52] U.S. Cl. .......................... 128/671; 128/670; 128/668; 395/23
[58] Field of Search ...................... 395/21, 23; 128/670, 128/668, 671, 713, 672

[56] References Cited

U.S. PATENT DOCUMENTS

| | | |
|---|---|---|
| 4,642,769 | 2/1987 | Petrofsky . |
| 5,465,321 | 11/1995 | Smyth ........................................ 395/22 |
| 5,509,424 | 4/1996 | Al-Ali ........................................ 128/713 |
| 5,542,430 | 8/1996 | Farrugia et al. ........................... 128/705 |
| 5,579,778 | 12/1996 | Baker et al. ............................... 128/713 |
| 5,584,291 | 12/1996 | Vapola et al. ............................. 128/670 |
| 5,590,665 | 1/1997 | Kanai ........................................ 128/920 |

OTHER PUBLICATIONS

Cardiovascular Diagnostics, Technology Brief, 94–11–1.

*Primary Examiner*—William E. Kamm
*Assistant Examiner*—Kennedy J. Schaetzle
*Attorney, Agent, or Firm*—Paul W. Zimmerman

[57] ABSTRACT

The present invention is a method of diagnosing a cardiopulmonary condition in an individual by comparing data from a progressive multi-stage test for the individual to a nonlinear multi-variate model, preferably a recurrent artificial neural network having sensor fusion. The present invention relies on a cardiovascular model developed from physiological measurements of an individual. Any differences between the modeled parameters and the parameters of an individual at a given time are used for diagnosis.

13 Claims, 8 Drawing Sheets

ARTIFICIAL NEURAL NETWORK CARDIOPULMONARY MODELING AND DIAGNOSIS

This invention was made with Government support under Contract DE-AC06-76RLO 1830 awarded by the U.S. Department of Energy. The Government has certain rights in the invention.

FIELD OF THE INVENTION

The present invention relates to automated diagnosis of cardiopulmonary condition of an individual. More specifically, the invention relates to the use of model based reasoning in analysis of progressive multi-stage test data for the diagnosis.

BACKGROUND OF THE INVENTION

Medical diagnosis and in particular cardiopulmonary diagnosis is limited by the ability of a physician or medical team to assimilate all of the relevant data including relationships between multiple parameters including but not limited to height, age, weight, gender, and internal heart rate and blood pressures as a function of exertion. Conventional modeling techniques are based upon generic models with possibly a few free variables that fit the model to an instance of a system. For example, a respiratory system model-based on differential equations may have a few free variables adjusted to an individual's gender, age, and weight. Conventional diagnostic techniques most often require that the differences between the modeled and actual data are known a-priori to the person developing the diagnostic system. These techniques are handicapped by both the ability of the person to understand the diagnostic differences in the data and by the applicability of those differences to the modeling technique. Physicians have learned to rely upon limited parameter analysis for diagnosis. For example, for a given age and weight of an individual, the physician may rely on a deterministic mathematical formula that was developed from statistical observation of hundreds and thousands of people. However, comparing an individual to a bulk average does not permit consideration of other variables that may be significant to determining an individual's medical condition. Accordingly, the computational capacity of computers has been exploited to aid a physician in making diagnoses. Differential equations, hidden Markov models, rule based systems and artificial neural networks have all been used in one form or another for data reduction and presentation to aid physicians.

An artificial neural network (ANN) is an algorithmic system implemented in either software or hardware. An ANN-based model is potentially a superior model because almost all of its free variables are adjustable to behave as a specific instance of a system and because less a-priori knowledge is needed. The concept of ANNs was inspired by the way the biological brain processes information. ANNs, like people, learn by example. Learning in the biological brain occurs in a network of neurons that are interconnected by axons. A point of contact (actually most often a narrow gap) between an axon from one neuron to another is called a synapse. Learning is a matter of adjusting the electrochemical connectivity across these synapses.

An ANN is a network of neurons or processing elements (PE) and weighted connections. The connections correspond to axons and the weights to synapses in the biological brain. A PE performs two functions. It sums the inputs from several incoming connections and then applies a transfer function to the sum. The resulting value is propagated through outgoing connections to other PEs. Typically, these PEs are arranged in layers; with the input layer receiving inputs from the real-world and each succeeding layer receiving weighted outputs from the preceding layer as its input. Hence the creation of a feed forward ANN in which each input is fed forward to its succeeding layer. The first and last layers in this ANN configuration are typically referred to as input and output layers. (Input-layer PEs are not true PEs in that they do not perform a computation on the input.) Any layers between the input and output layers (usually 0–2 in number) are called hidden layers because they do not have contact with any real-world input or output data.

In addition to simple feedforward ANNs, some feedforward ANNs are recurrent ANNs. These networks have feedback connections that move intermediately processed data or output data back to previous layers. These feedback connections allow the ANNs to capture temporal information in data and, thus, model dynamic systems.

Back propagation is one of several possible learning rules to adjust the connection weights during supervised learning (learning by example). Learning occurs when the network weights are adjusted as a function of the error found in the output of the network. The error is the difference between the expected output and the actual output. The weights are adjusted backwards (back-propagated) through the ANN network until the error is minimized for a set of training data.

ANNs have been applied to an increasing number of real-world problems of considerable complexity. Their most important advantage is in solving problems that are too complex for conventional technologies; that is, problems that do not have an algorithmic solution or for which an algorithmic solution is too complex to be found. In general, because of their abstraction from the biological brain, ANNs are well suited to problems that people are good at solving, but for which computers are not. These problems include pattern recognition, modeling, and forecasting (which requires the recognition of trends in data).

In the medical field, ANN has been used to aid in imaging, for example, imaging of pap smears for identification of malignant cells. These systems have been developed to catalog or classify a cell as to whether or not the cell is malignant. In these systems, cell classification is independent from the characteristics of an individual and is simply visual characteristics of the cell in question. A classification system, in general, lacks the capability to identify time related trends.

Another example is the paper by G. Dorffner, E. Leitgeb, H. Koller. 1994. "Toward Improving Exercise ECG for Detecting Ischemic Heart Disease with Recurrent and Feedforward Neural Nets." *Proceedings of the IEEE Workshop on Neural Networks in Signal Processing*. Ermioni, Greece. This system is also a classification system that is unable to identify time related trends for an individual.

SUMMARY OF THE INVENTION

The present invention is a method of diagnosing a cardiopulmonary condition in an individual by comparing data from a progressive multi-stage test for the individual to a non-linear multi-variate model, preferably a recurrent artificial neural network providing sensor fusion. The present invention relies on a cardiovascular model developed from physiological measurements of an individual. Any differences between the modeled parameters and the parameters of an individual at a given time are used for diagnosis.

The present invention uses a model as a basis for diagnosis with "model-based reasoning." A diagnostic system that uses model-based reasoning compares actual data to modeled data and exploits the differences for diagnosis. Two prerequisites for this methodology to be successful are that (i) the model(s) is/are authentic to the system(s) being diagnosed and (ii) the differences between the modeled data and the actual data are known for healthy and diseased or unhealthy conditions. The diagnostic system will analyze the current physiological measurements using all relevant models for describing the medical condition of the individual. The invention will generate a comprehensive diagnosis for an individual based on both an individual's model, if existing, and generic models. The models developed are especially interesting because they allow detection of trends in an individual's medical condition. These individual models also make this diagnostic approach more sensitive for recognizing changing medical conditions. If no previous test data exists for an individual, then the diagnosis is based on only generic models which are narrowly defined according to the demographic data of the individual being tested.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

Figure 1:
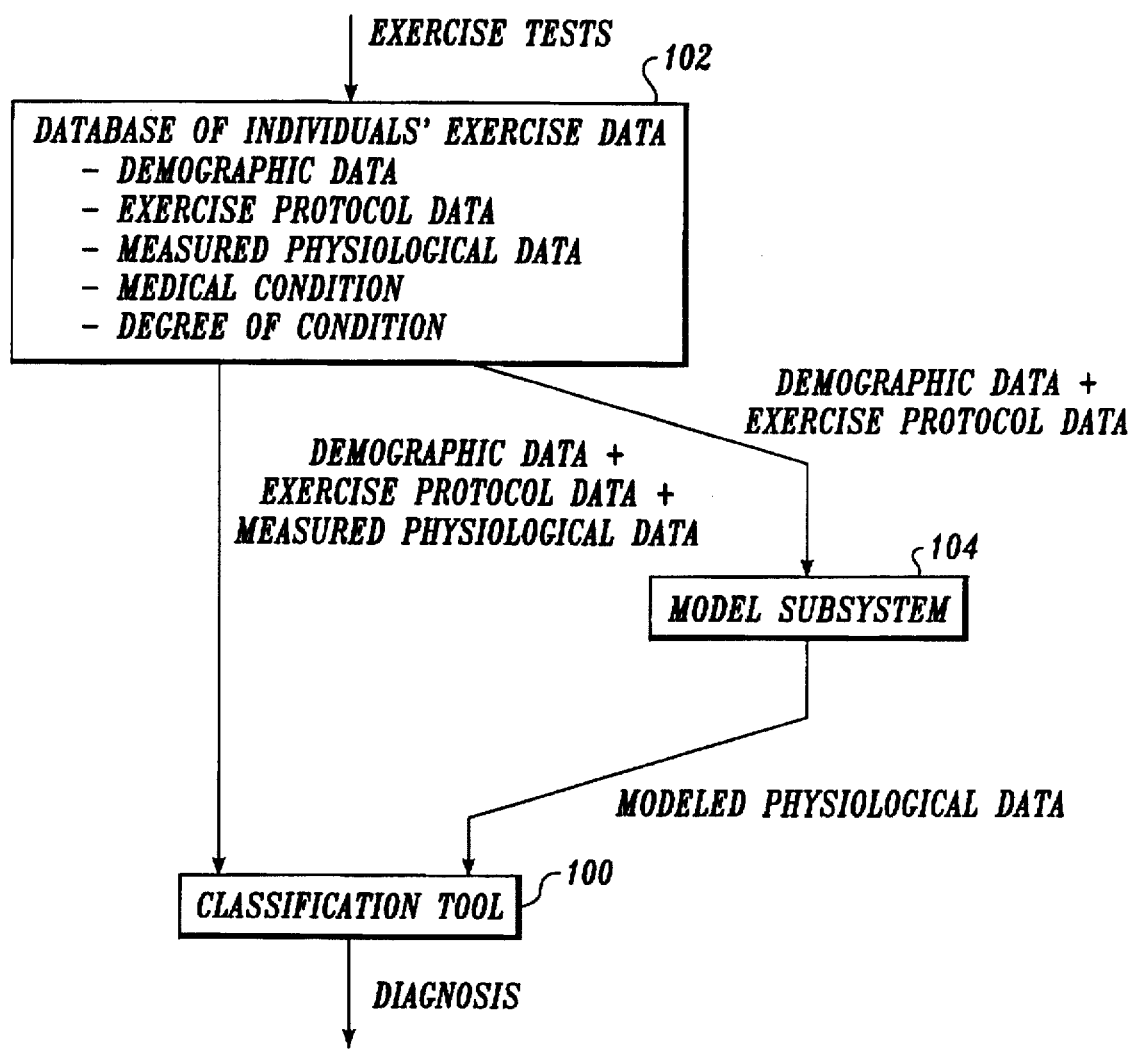
FIG. 1 is a diagram of development of a classification tool.

The present invention is a method of diagnosing a cardiopulmonary condition of a test individual, having the steps of:

(a) cataloging at least one demographic parameter for the test individual;

(b) subjecting the test individual to a progressive multi-stage test and collecting at least one test physiological parameter as a function of time, together with at least one progressive multi-stage test operating parameter as a function of time;

(c) entering the demographic parameter(s) together with progressive multi-stage test operating parameter(s) as a function of time into a non-linear multi-variate cardiopulmonary model for a healthy individual and obtaining at least one modeled physiological parameter as a function of time for the healthy individual;

(d) obtaining a result vector as a function of time of a result of the measured physiological parameter(s) from the test individual combined with the modeled physiological parameter(s); and (e) comparing the result vector to at least one vector of results known to represent at least one specific cardiopulmonary condition of at least one diseased individual having at least one demographic parameter in common with or similar to the test individual and determining the cardiopulmonary condition of the test individual. It is preferred that the test individual be compared to generic data from individuals having a similar demographic makeup.

A demographic parameter includes but is not limited to height, weight, age, gender, national origin, and geographical region of residence and combinations thereof.

Physiological parameters include but are not limited to heart rate, breathing rate, diastolic and systolic blood pressure.

A progressive multi-stage test may be a graded exercise test or cardiovascular stress test that may be carried out on an exertion test apparatus including but not limited to treadmill, exercycle, and stair step. Progressive multi-stage test parameters include the exercise test protocol of intensity and duration of the physical effort as may be measured, for example, by a slope of a treadmill track, cadence of step and amount of time.

The non-linear multi-variate model maps the exercise protocol data and the individual's demographic data to the physiological measurements for each exercise test data set. When multiple data sets are used in the development of one model, then the parametric relationship is captured between the two sides of the data mapping. The captured relationship is subsequently used to generate modeled physiological "measurements" for a given set of exercise protocol data and demographic data.

The non-linear multi-variate model (model) subsystem is capable of developing generic models and individual models. The generic models are made from data of individuals identified as healthy. A generic model may include data for any individual or it may be specific to one or more demographic parameters, for example all males, all females, different age groups and combinations thereof. Preferably, the generic models would be based on many hundreds of individuals so that 'the models could provide statistically significant results when it is desired to limit the comparison by one or more demographic parameters.

An individual model is made from data from a particular individual. The individual, of course, may be healthy or diseased. A model of an individual's cardiovascular system, however, mimics the relationship among physiological parameters (i.e., heart rate, systolic and diastolic blood pressures, and breathing rate) at different physical activity levels specifically for that individual. When a model is adapted to an individual, then it becomes a model of the physical condition of that individual. A model for an individual can be compared to the actual measurements of that individual at a later time. Any differences can be exploited to evaluate and diagnose medical conditions that affect the cardiovascular system of that individual. When used in clinical exercise testing (e.g., graded exercise tests), these cardiovascular models increase the sensitivity of correctly diagnosing several medical conditions such as those listed in Table 1. These models will also increase the sensitivity of detecting or excluding several other conditions that cannot be uniquely diagnosed in an exercise test alone such as those listed in Table 2.

Table 1: Conditions detectable with exercise testing myocardial ischemia peripheral vascular disease exercise-induced asthma vasoregulatory asthenia unfitness vasoregulatory asthenia psychogenic dyspnea muscle phosphorylase deficiency Table 2: Conditions not directly detectable with exercise testing alone.

chronic bronchitis pulmonary emphysema pulmonary infiltration, alveolitis, and fibrosis pulmonary thromboelism and hypertension congenital cardiac abnormalities cardiac valvular obstruction or incompetence primary myocardial disease generalized neuromuscular disorders The non-linear multi-variate model is preferably defined within an artificial neural network (ANN). Recurrent ANNs are preferred for the cardiovascular modeling application to capture the temporal information in physiological parameters. These physiological parameters are time-series data from which both the absolute values and the rates of change need to be modeled. Recurrent ANNs recycle a small portion of information from time t−1 at time t. Indirectly, decreasing portions of information from time t−2, t−3, t−4, etc. are also captured, thus enabling recurrent ANNs to model the temporal dynamics in data.

The first time that an individual is tested, the test data may be compared to a previously developed generic model based upon tests from at least one healthy individual and at least one diseased individual for each disease state to be diagnosed.

The result vector is the outcome of a mathematical combination of modeled and measured physiological variables. The mathematical combination may be a subtracted difference, a divided ratio or more complex mathematical combination involving single or multiple mathematical operations.

Constructing the non-linear multi-variate cardiopulmonary model has the steps of:

(a) cataloging at least one demographic parameter for at least one individual;

(b) subjecting the at least one individual to a progressive multi-stage test and collecting at least one physiological parameter as a function of time, and obtaining at least one progressive multi-stage test operating parameter as a function of time;

(c) entering the demographic parameter(s) and physiological parameter(s) together with the progressive multi-stage test operating parameter(s) into a non-linear multi-variate modeling system; and (d) building the non-linear multi-variate model for the tested individual(s).

The model is then able to receive at least one demographic parameter and from that demographic parameter together with at least one progressive multi-stage test operating parameter, the model provides at least one physiological parameter as a function of time. Before a particular individual has been tested, the model is based upon data from previously tested healthy individuals. The model may also be based upon one or more of the various work models that have been developed to predict physiological parameters as a function of time. After an individual has been tested once, subsequent test data may be compared to the individual's n−1 previous test(s) thereby providing a more accurate individualistic profile for the individual than has been previously possible.

The diagnostic system of the present invention does require a classification subsystem. The purpose of the classification subsystem is to recognize any medical condition, in an individual, from a set of predefined medical conditions. The development of the classification subsystem uses the modeled physiological parameters from the modeling subsystem together with the measured physiological parameters data acquired during exercise tests to obtain result vectors of the combination of the modeled physiological parameters and the measured physiological parameters as shown in FIG. 1. A multi-variate analysis method in the classification tool 100 is developed to map the exercise test data and the modeled data from the modeling subsystem to known medical conditions. The captured relationship between the exercise data 102, modeled data, and the information about medical conditions is subsequently used to diagnose unknown medical conditions from later exercise tests. Unlike previous classification systems, the classification subsystem of the present invention is based upon output from a model 104 so that model based reasoning is employed in the diagnosis. The vectors representing physiological deviations may be computed by subtracting the modeled physiological data vectors from the measured physiological data vectors at time t, time t+1, etc. along the length of the exercise test. For example, if the measured heart rate, at the first six time steps, is the vector {73, 78, 83, 87, 91, 95} and the modeled heart rate is {70, 77, 81, 85, 88, 91}, then the result vector for the heart is {73−70, 78−77, 83−81, 87−85, 91−88, 95−91} or {3, 1, 2, 2, 3, 4}.

The classification subsystem of the present invention is constructed wherein at least one set of results known to represent at least one specific cardiopulmonary condition is obtained by the steps of:

(a) cataloging at least one demographic parameter for a diseased individual having the at least one specific cardiopulmonary condition;

(b) subjecting the diseased individual(s) to a progressive multi-stage test and collecting at least one physiological parameter as a function of time together with at least one progressive multi-stage test parameter;

(c) entering the demographic parameter(s) together with the progressive multi-stage test parameter(s) into the non-linear multi-variate modeling system;

(d) obtaining a result vector of a combination of physiological parameters from the diseased individual with the cardiopulmonary multi-variate model for at least one healthy individual of similar demographic parameters; and (e) storing the result vector.

Thus, in the present invention, differences in the form of the result vector from a "normal" or "healthy" model are stored for classification comparison. To the extent that classification may benefit from additional information, "raw" data from the exertion test may be combined with the result vector.

Figure 2A:
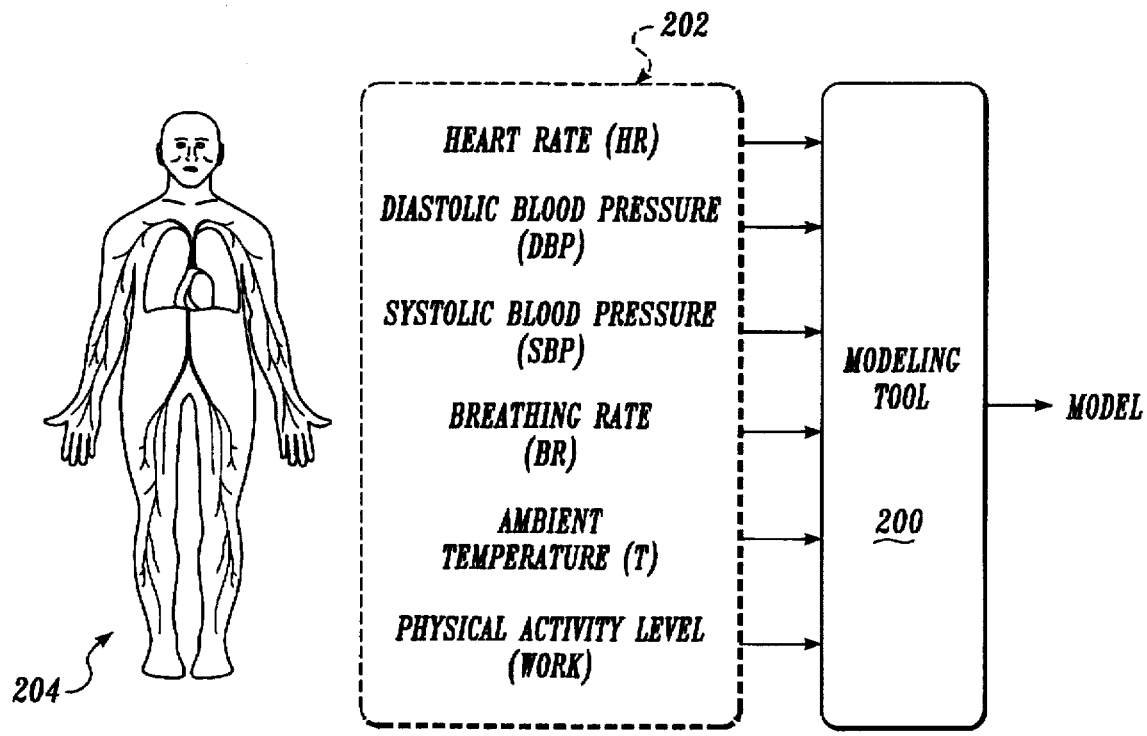
FIG. 2a is a diagram of an artificial neural network modeling tool.
Figure 2B:
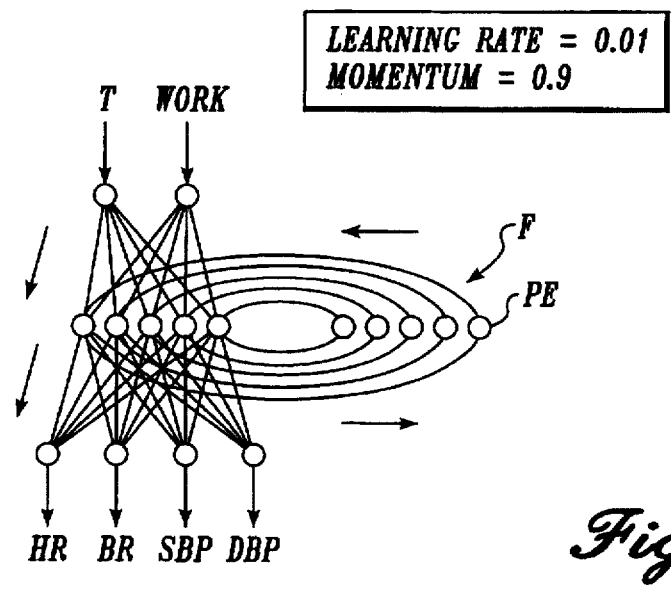
FIG. 2b is a diagram of an artificial neural network physiological model.

The modeling portion of the present invention is illustrated in FIGS. 2a and 2b. The modeling tool 200 is preferably an artificial neural network that receives a sequence of physiological parameters 202 from biomedical sensors (not shown) placed on an individual 204. The artificial neural network learns the temporal dynamics of the physiological parameters based upon progressive multi-stage parameters to produce an ANN-based cardiovascular model.

FIG. 2b illustrates a configuration of the ANN produced by the modeling tool. This ANN has two inputs, four outputs, and five hidden processing elements. The ANN takes the ambient temperature T and the physical activity W as input. The four outputs, heart rate HR, breathing rate BR, systolic blood pressure SBP, and diastolic blood pressure DBP, are clamped to the "actual" values during the training phase. For the initial cardiovascular model prototypes, the "actual" values are generated by a nonadaptive cardiovascular model. During the modeling phase, the temperature T and the work W are input to the ANN, and the values at the outputs are taken as the modeled parameters. The feedback links F going through the five processing elements PE on the right side of the ANN enable it to capture temporal information in the data.

Figure 3:
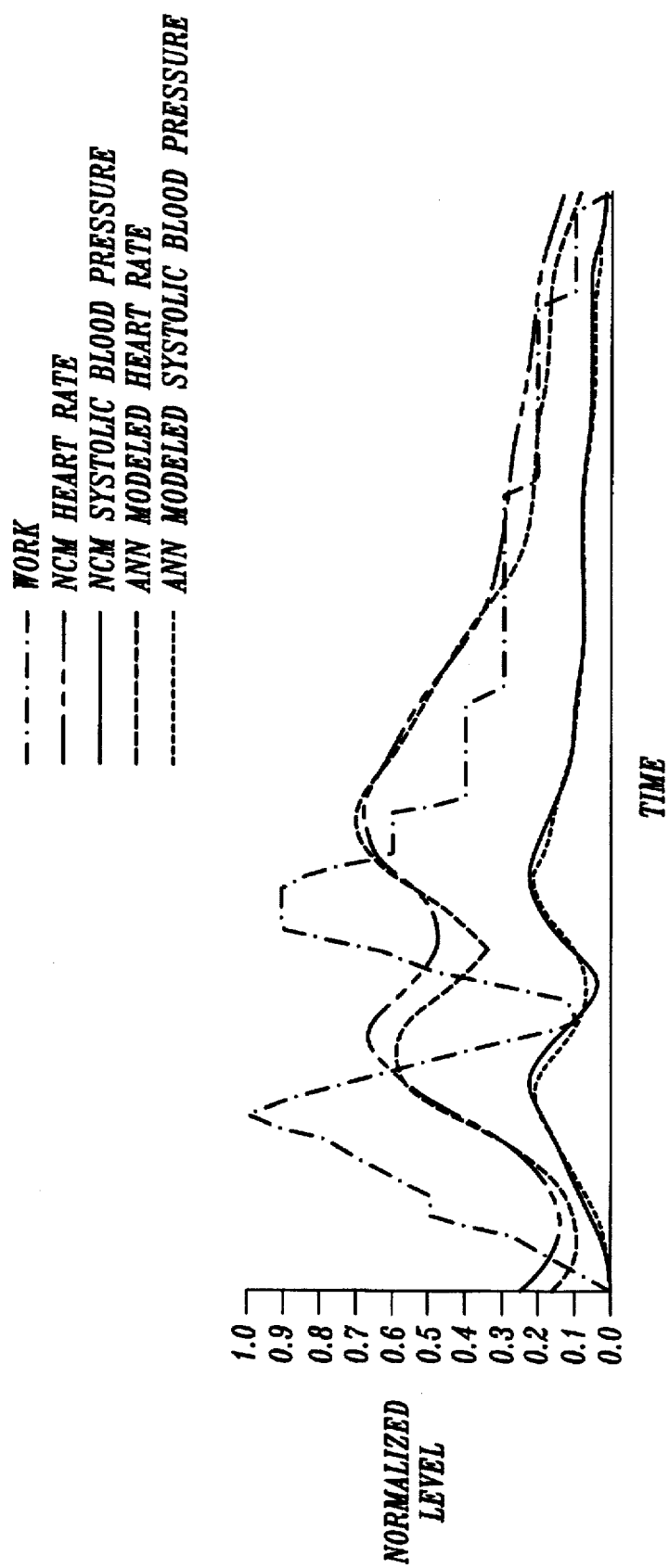
FIG. 3 is a graph of physiological parameters versus time for non-adaptive cardiovascular model (NCM) and artificial neural network (ANN) model responses.
Figure 4A:
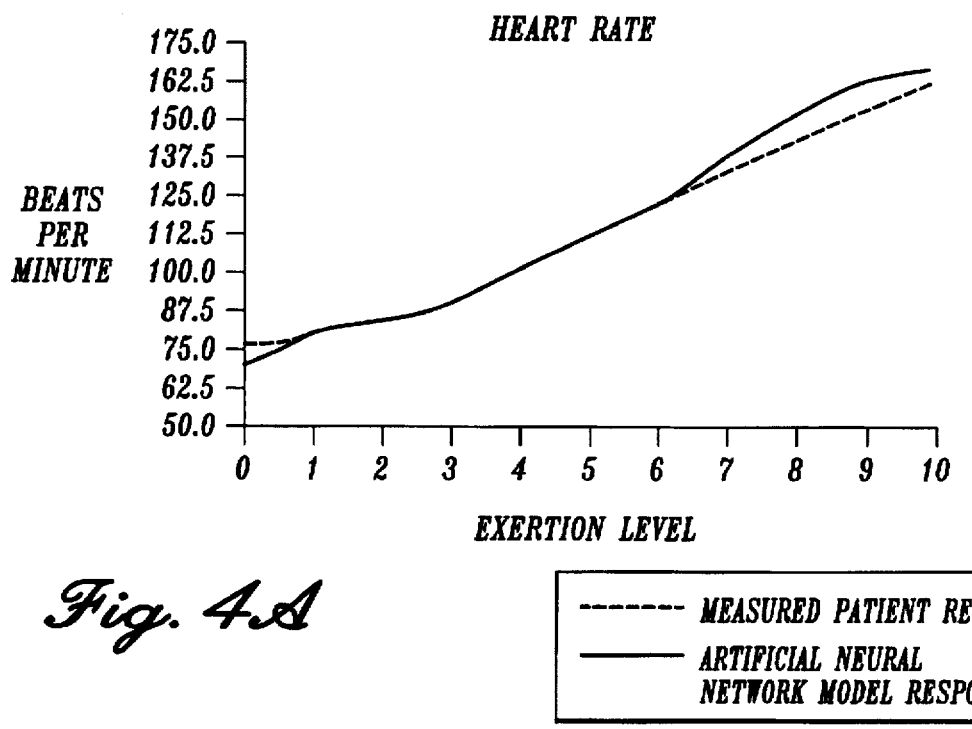
FIG. 4a is a graph of heart rate versus exertion level.
Figure 4B:
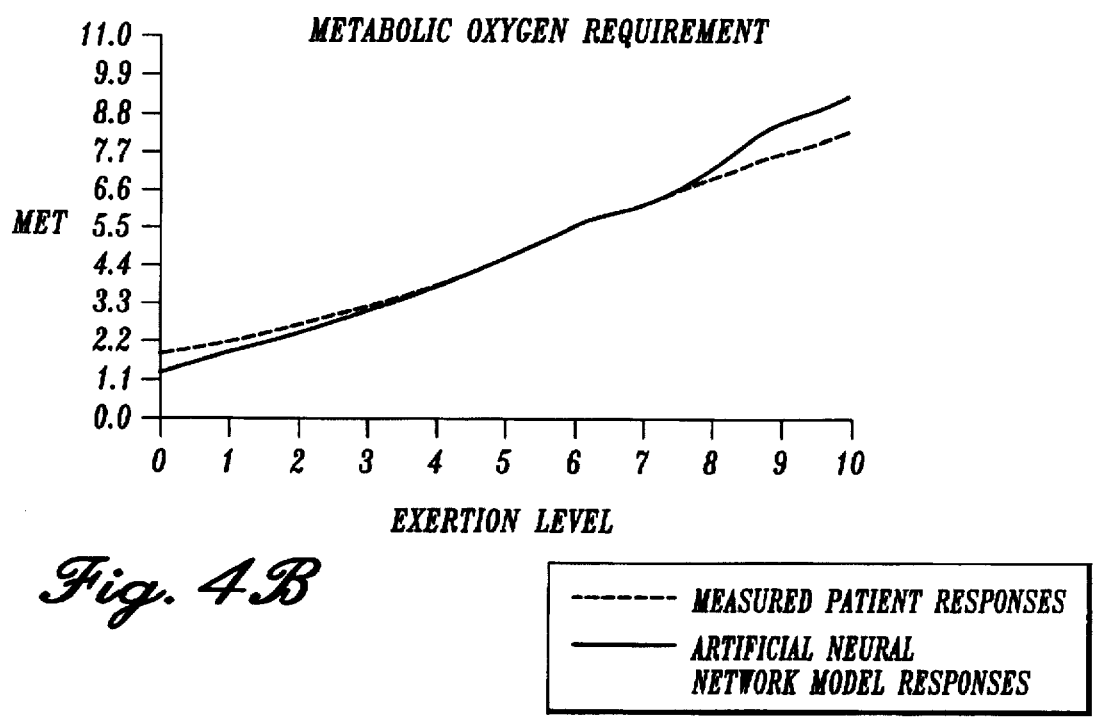
FIG. 4b is a graph of metabolic oxygen requirement versus exertion level.
Figure 4C:
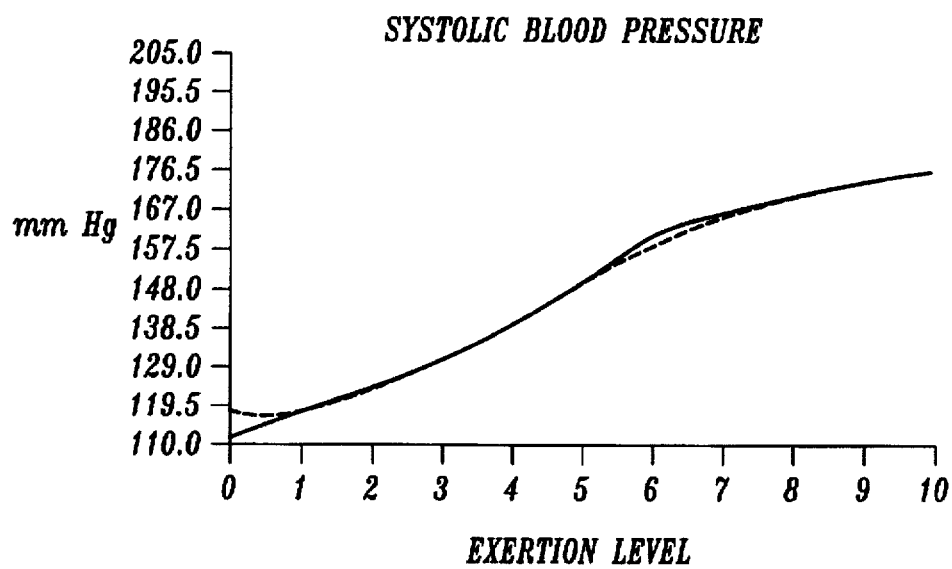
FIG. 4c is a graph of systolic blood pressure versus exertion level.
Figure 4D:
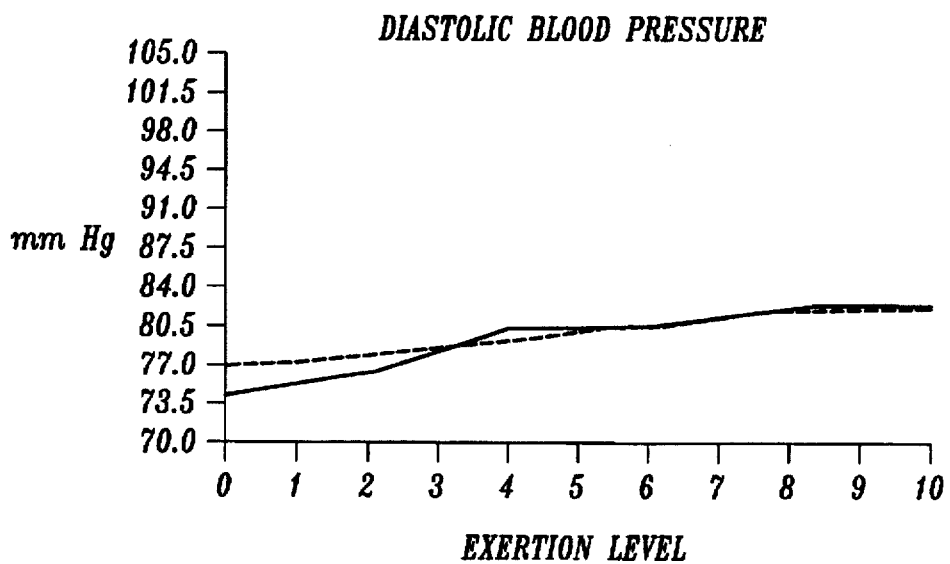
FIG. 4d is a graph of diastolic blood pressure versus exertion level.
Figure 4E:
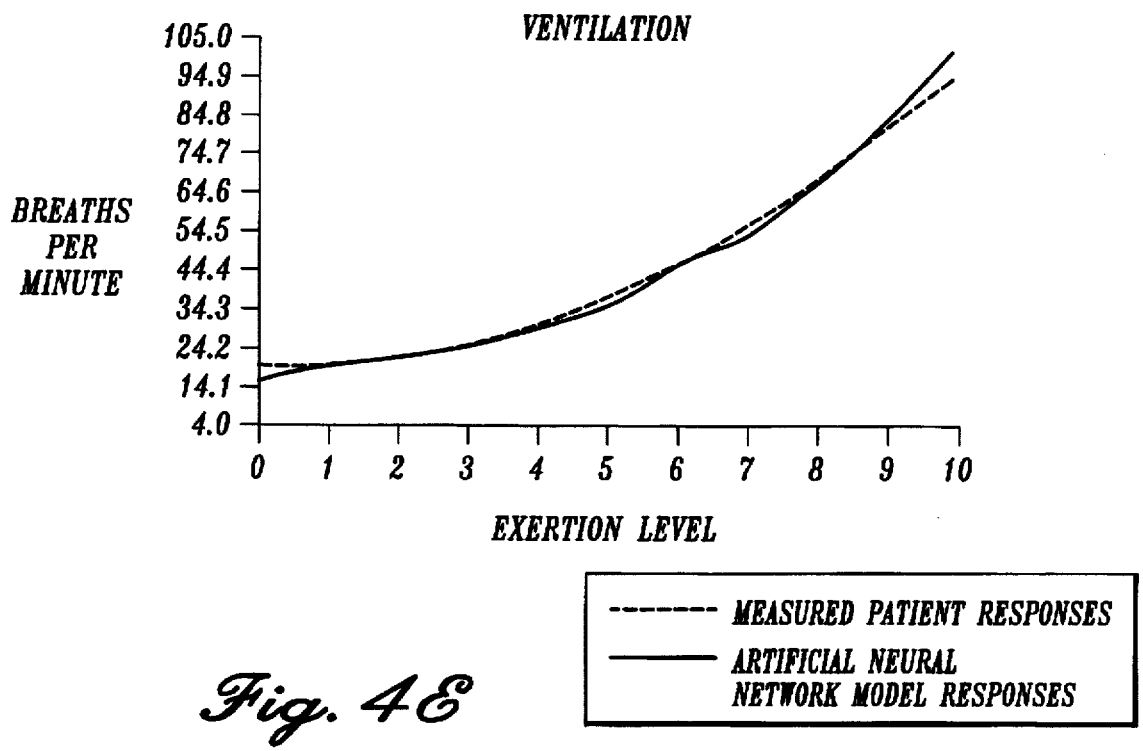
FIG. 4e is a graph of ventilation versus exertion level.
Figure 4F:
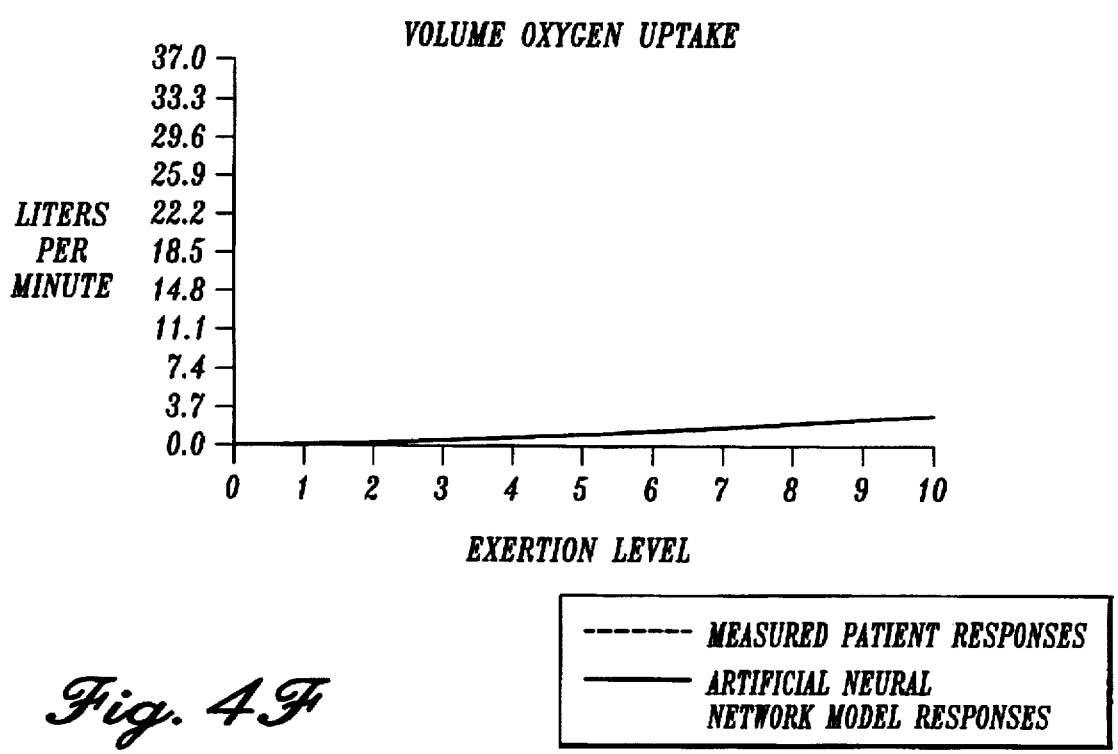
FIG. 4f is a graph of volume oxygen uptake versus exertion level.
Figure 4G:
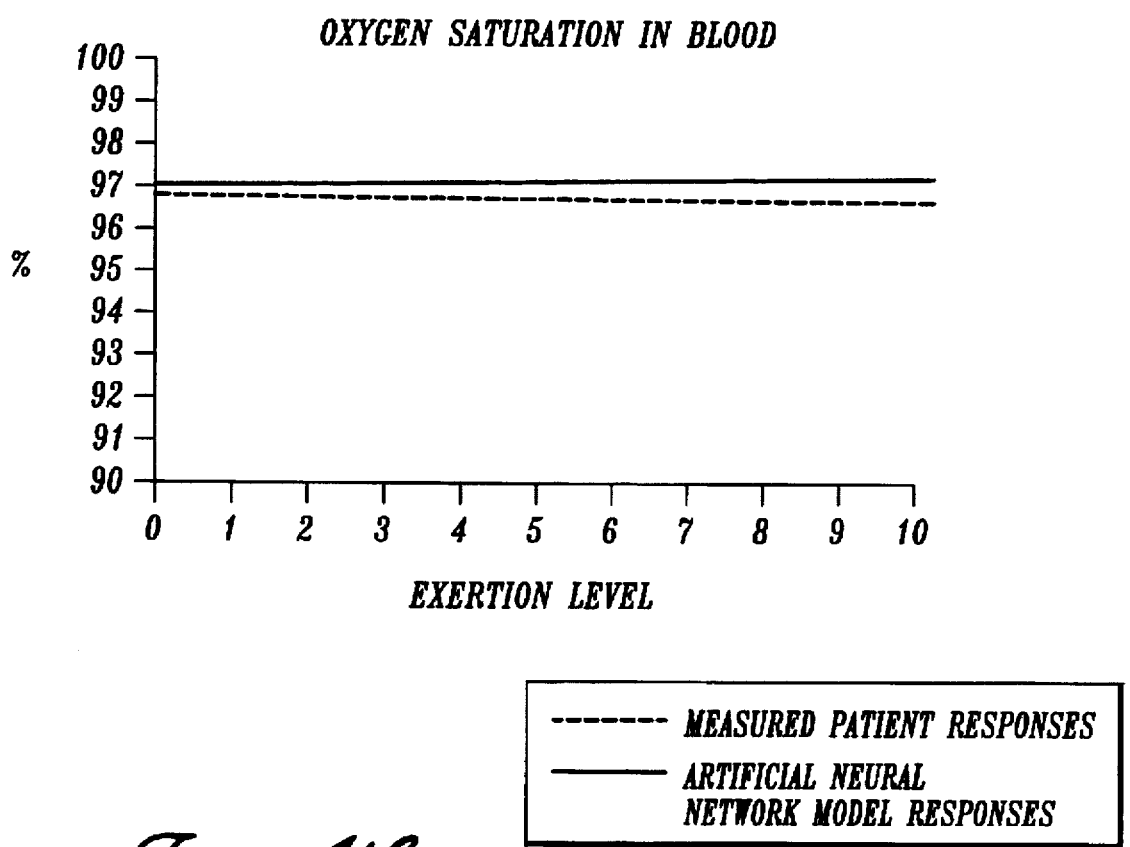
FIG. 4g is a graph of oxygen saturation in blood versus exertion level.

After development of the model, the model generates physiological responses for simulations with varying levels of physical activity at specified temperature(s). FIG. 3 shows how the parameters modeled with the ANN compare with the physiological parameters generated with a nonadaptive cardiovascular model NCM. This NCM has been used for creating data with sufficient complexity for the development of the ANN modeling tool.

EXAMPLE 1

An experiment was conducted to demonstrating the non-linear multi-variate modeling. An artificial neural network model was built using three progressive multi-stage tests for the same individual with the tests separate in calendar time by about 1 year between each test. A fourth progressive multi-stage test was performed with the same individual for comparison to the individual's three-test baseline.

Results are shown in FIGS. 4a–4g. Physiological variables of heart rate, metabolic oxygen requirement, systolic blood pressure, diastolic blood pressure, ventilation (breathing rate), volume oxygen uptake, and oxygen saturation in blood are measured as a function of exertion level. From these results, one may identify differences in the data of the fourth test (broken lines) compared with the model based upon the first three (solid lines). A combination, for example a mathematical difference vector may be obtained from these results for subsequent diagnosis.

Diagnosis

Figure 5:
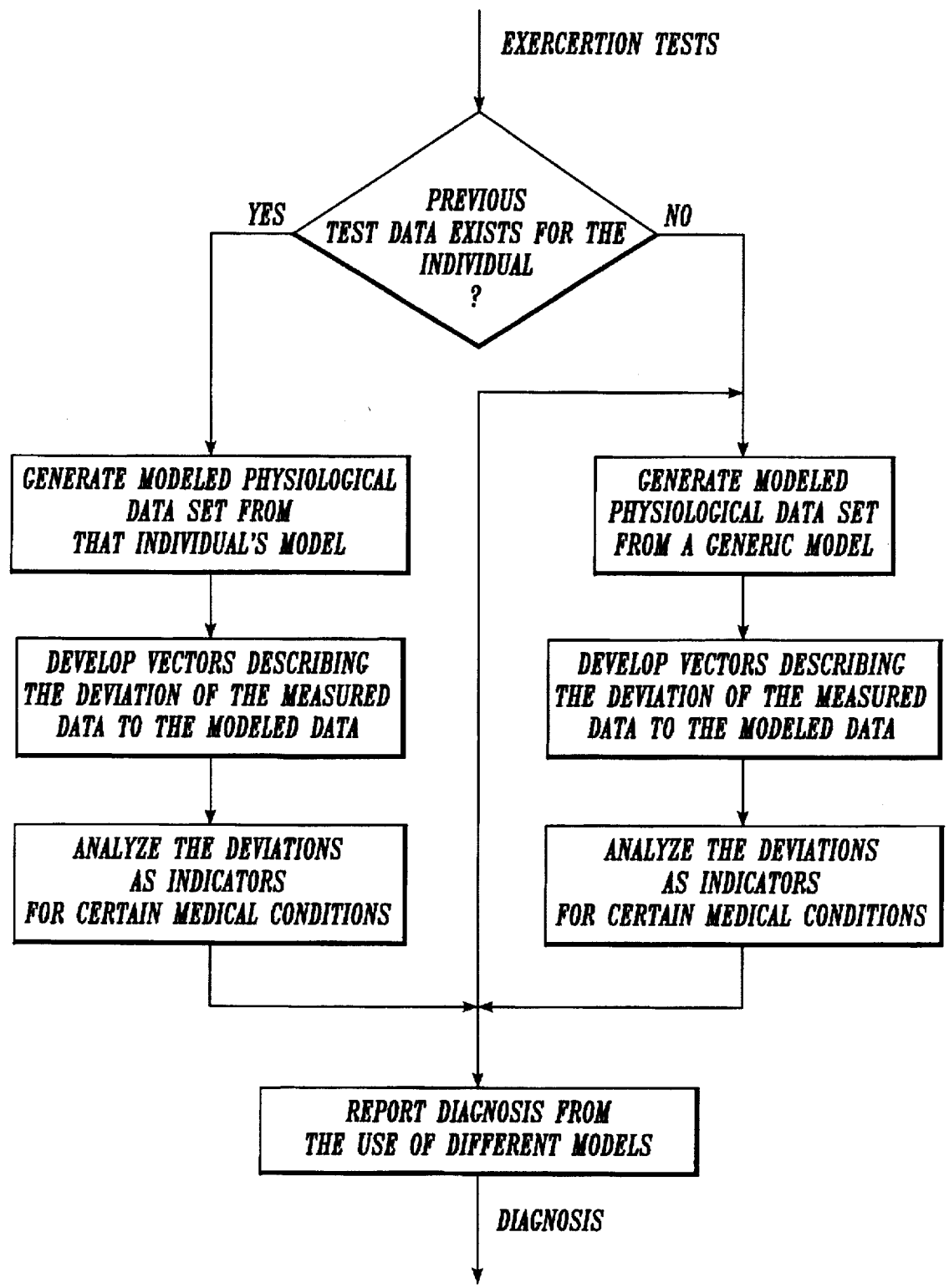
FIG. 5 is a flow chart of the present invention.

The invention will generate a comprehensive diagnosis for an individual based on both an individual's model, if existing, and generic models. When multiple data sets are used in the development of one model, then the parametric relationship is captured between the two sides of the data mapping. The captured relationship is subsequently used to generate modeled physiological "measurements" for a given set of exercis protocol data and demographic data. FIG. 5 summarizes the steps from exertion tests and final diagnosis.

Alternative Embodiments

A cardiovascular model can be incorporated into an automatic, continuous diagnostic system carried by an individual. Physiological parameters received from noninvasive biomedical sensors can be compared with the modeled parameters in real-time. This real-time diagnosis of an individual's general health increases the possibility of early detection of undesired medical conditions and reduces the response time of medical help for people working in hazardous and dangerous environments, (e.g., soldiers, law enforcement officers, and emergency response personnel, for example firemen). A real-time diagnostic system further enables continuous monitoring of individuals with medical conditions in nursing homes and in home-care situations. Reduction of the response time for medical help is critical in minimizing medical complications and the loss of life.

Individuals working in hazardous environments may be monitored for early diagnoses of a degradation in health. The working environment and other causes may contribute to this degradation and make an employee unsuitable for certain work. For example, the present invention may be used to aid fire districts in determining the health effects from smoke inhalation on individual firemen. The diagnosis would determine whether firemen have recovered sufficiently from a previous inhalation of smoke permitting entry into smoke-filled environments again.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method of diagnosing a cardiopulmonary condition of a test individual, comprising the steps of:

(a) cataloging at least one demographic parameter for the test individual;

(b) subjecting the test individual to a progressive multi-stage test and collecting at least one actual physiological parameter as a function of time, together with at least one progressive multi-stage test operating parameter as a function of time;

(c) entering the demographic parameter(s) together with progressive multi-stage test operating parameter(s) as a function of time into a non-linear multi-variate cardiopulmonary model for a healthy individual and obtaining at least one modeled physiological parameter as a function of time for the healthy individual;

(d) obtaining a result vector as a function of time of a combination of the actual physiological parameter(s) from the test individual mathematically combined with the modeled physiological parameter(s); and (e) comparing the result vector to at least one vector of results known to represent at least one specific cardiopulmonary condition of at least one diseased individual having at least one demographic parameter similar to the test individual and determining the cardiopulmonary condition of the test individual.

2. The method as recited in claim 1, wherein constructing the non-linear multi-variate cardiopulmonary model comprises the steps of:

(a) cataloging at least one demographic parameter for at least one individual;

(b) subjecting the at least one individual to a progressive multi-stage test and collecting at least one physiological parameter as a function of time, and obtaining at least one progressive multi-stage test operating parameter as a function of time;

(c) entering the demographic parameter(s) and physiological parameter(s) together with the progressive multi-stage test operating parameter(s) into a non-linear multi-variate modeling system; and (d) building the non-linear multi-variate model for the tested individual(s).

3. The method as recited in claim 2, wherein said at least one vector of results known to represent at least one specific cardiopulmonary condition is obtained comprising the steps of:

(a) cataloging at least one demographic parameter for a diseased individual having the at least one specific cardiopulmonary condition;

(b) subjecting the diseased individual(s) to a progressive multi-stage test and collecting at least one physiological parameter as a function of time together with at least one progressive multi-stage test parameter;

(c) entering the demographic parameter(s) together with the progressive multi-stage test parameter(s) into the non-linear multi-variate modeling system;

(d) obtaining a result vector of a mathematical combination of physiological parameters from the diseased individual combined with the cardiopulmonary multi-variate model for at least one healthy individual of similar demographic parameters; and (e) storing the result vector.

4. The method as recited in claim 1, wherein said non-linear multi-variate cardiopulmonary model is a trained artificial neural network.

5. The method as recited in claim 1, wherein said comparing is done within a trained artificial neural network.

6. The method as recited in claim 5, wherein said artificial neural network is a feed forward artificial neural network with a recurrent layer.

7. The method as recited in claim 1, wherein the non-linear multi-variate cardiopulmonary model is a generic model.

8. The method as recited in claim 1, wherein the non-linear multi-variate cardiopulmonary model is an individual model.

9. The method as recited in claim 1, wherein the result vector is a signed difference vector of mathematical differences of a measured physiological parameter subtracted from a modeled physiological parameter.

10. The method as recited in claim 10, wherein the measured and modeled physiological parameters are functions of time.

11. A method of diagnosing a cardiopulmonary condition of a test individual, comprising the steps of:

(a) cataloging at least one demographic parameter for the test individual;

(b) subjecting the test individual to a progressive multi-stage test and collecting at least one tested physiological parameter as a function of time, together with at least one progressive multi-stage test operating parameter as a function of time;

(c) entering the demographic parameter(s) together with progressive multi-stage test operating parameter(s) as a function of time into a non-linear multi-variate cardiopulmonary model for a healthy individual and obtaining at least one modeled physiological parameter as a function of time for the healthy individual, said non-linear multi-variate cardiopulmonary model constructed by (i) cataloging at least one demographic parameter for at least one model individual;

(ii) subjecting the at least one model individual to a model progressive multi-stage test and collecting at least one model physiological parameter as a function of time, and obtaining at least one model progressive multi-stage test operating parameter as a function of time;

(iii) entering the model demographic parameter(s) and model physiological parameter(s) together with the model progressive multi-stage test operating parameter(s) into a non-linear multi-variate modeling system; and (iv) building the non-linear multi-variate model for the modeled individual(s)

(d) obtaining a signed difference vector as a function of time of differences of the actual physiological parameter(s) from the test individual subtracted from the modeled physiological parameter(s); and (e) comparing the signed difference vector to at least one vector of differences known to represent at least one specific cardiopulmonary condition of at least one diseased individual having at least one demographic parameter in common with the test individual and determining the cardiopulmonary condition of the test individual, said at least one vector of differences obtained by (i) cataloging at least one demographic parameter for a diseased individual having the at least one specific cardiopulmonary condition;

(ii) subjecting the diseased individual(s) to a progressive multi-stage test and collecting at least one diseased physiological parameter as a function of time together with at least one diseased progressive multi-stage test parameter;

(iii) entering the diseased demographic parameter(s) together with the diseased progressive multi-stage test parameter(s) into the non-linear multi-variate modeling system;

(iv) obtaining a difference vector of differences of diseased physiological parameters subtracted from the cardiopulmonary multi-variate model for at least one healthy individual of similar demographic parameters; and (v) storing the difference vector.

12. The method as recited in claim 11, wherein said non-linear multi-variate cardiopulmonary model is a trained artificial neural network.

13. The method as recited in claim 11 wherein said comparing is done within a trained artificial neural network.

* * * * *